United States Patent
Kato et al.

(10) Patent No.: US 7,407,822 B2
(45) Date of Patent: Aug. 5, 2008

(54) METHOD FOR INSPECTING INSULATING FILM FOR FILM CARRIER TAPE FOR MOUNTING ELECTRONIC COMPONENTS THEREON, INSPECTION APPARATUS FOR INSPECTING THE INSULATING FILM, PUNCHING APPARATUS FOR PUNCHING THE INSULATING FILM, AND METHOD FOR CONTROLLING THE PUNCHING APPARATUS

(75) Inventors: Kazuyoshi Kato, Shimonoseki (JP); Naoaki Horiai, Shimonoseki (JP)

(73) Assignee: Mitsui Mining & Smelting Co., Ltd., Tokyo (JP)

( * ) Notice: Subject to any disclaimer, the term of this patent is extended or adjusted under 35 U.S.C. 154(b) by 41 days.

(21) Appl. No.: 11/109,874

(22) Filed: Apr. 20, 2005

(65) Prior Publication Data

US 2005/0243310 A1    Nov. 3, 2005

(30) Foreign Application Priority Data

Apr. 30, 2004   (JP) .............................. 2004-135365

(51) Int. Cl.
*G01R 31/26* (2006.01)
*H01L 21/66* (2006.01)

(52) U.S. Cl. ................... 438/16; 438/15; 257/E21.521; 257/E21.524; 257/E21.526

(58) Field of Classification Search ................... 438/14
See application file for complete search history.

(56) References Cited

U.S. PATENT DOCUMENTS

| | | | | |
|---|---|---|---|---|
| 4,737,845 A | * | 4/1988 | Susuki et al. | 348/87 |
| 4,851,902 A | * | 7/1989 | Tezuka et al. | 348/126 |
| 5,113,565 A | * | 5/1992 | Cipolla et al. | 29/25.01 |
| 5,383,776 A | * | 1/1995 | Trail et al. | 425/135 |
| 5,598,345 A | * | 1/1997 | Tokura | 716/4 |
| 5,975,178 A | * | 11/1999 | Otsuka et al. | 156/358 |

(Continued)

FOREIGN PATENT DOCUMENTS

JP   10-288586 A   10/1998

(Continued)

*Primary Examiner*—Matthew S. Smith
*Assistant Examiner*—Jarrett J Stark
(74) *Attorney, Agent, or Firm*—Sughrue Mion, PLLC

(57) ABSTRACT

The invention provides an inspection apparatus and an inspection method for detecting defects, a punching apparatus, and a method for controlling a punching apparatus, for the purpose of immediate detection of debris from being lifted toward the surface of an insulating film for film carrier tape, which debris tends to occur during punching of the insulating film for film carrier tape by use of a punching mold, whereby the number of pieces having defects on the film surface caused by attachment of debris from being lifted or foreign matter is reduced to a minimum possible number. In the present invention, an insulating film for film carrier tape is irradiated with parallel rays having passed through a first polarizing filter, the insulating film having been punched and being conveyed; the rays having passed through or having been reflected by the insulating film for film carrier tape is caused to pass through a second polarizing filter; the rays having passed through the second polarizing filter, is received by means of an image pickup device; and the image input to the image pickup device is subjected to image processing as a difference of brightness, whereby defects of the insulating film for film carrier tape are detected.

6 Claims, 2 Drawing Sheets

U.S. PATENT DOCUMENTS

| | | | |
|---|---|---|---|
| 6,154,316 A | * | 11/2000 | Fukui et al. ................. 359/483 |
| 6,180,226 B1 | * | 1/2001 | McArdle et al. ............ 428/332 |
| 6,977,025 B2 | * | 12/2005 | McArdle et al. ......... 156/272.2 |
| 2003/0224540 A1 | * | 12/2003 | Watanabe et al. .............. 438/7 |
| 2004/0253818 A1 | * | 12/2004 | Okamoto et al. ............ 438/689 |
| 2005/0140975 A1 | * | 6/2005 | Sakai et al. ................. 356/369 |
| 2006/0258025 A1 | * | 11/2006 | Okamoto et al. .............. 438/14 |

FOREIGN PATENT DOCUMENTS

| | | |
|---|---|---|
| JP | 10-293018 A | 11/1998 |
| JP | 2000-351025 A | 12/2000 |

* cited by examiner

METHOD FOR INSPECTING INSULATING FILM FOR FILM CARRIER TAPE FOR MOUNTING ELECTRONIC COMPONENTS THEREON, INSPECTION APPARATUS FOR INSPECTING THE INSULATING FILM, PUNCHING APPARATUS FOR PUNCHING THE INSULATING FILM, AND METHOD FOR CONTROLLING THE PUNCHING APPARATUS

BACKGROUND OF THE INVENTION

1. Field of the Invention

The present invention relates to a method for inspecting insulating film (in the form of a long tape or sheet) for use in production of a film carrier tape for mounting electronic components thereon, such as a TAB (tape automated bonding) tape, a COF (chip on film) tape, a CSP (chip size package) tape, a BGA (ball grid array) tape, a μ-BGA (μ-ball grid array) tape, a FC (flip chip) tape, a QFP (quad flat package) tape, or an FPC (flexible printed circuit) tape (hereinafter such tapes are collectively referred to simply as film carrier tapes); to an inspection apparatus for detecting defects of an insulating film for film carrier tape for mounting electronic components thereon (hereinafter referred to simply as "an insulating film for film carrier tape"); to a punching apparatus for punching an insulating film for film carrier tape; and to a method for controlling a punching apparatus for punching an insulating film for film carrier tape. More particularly, the present invention relates to a method for inspecting an insulating film for film carrier tape-through employment of a light source of parallel rays, two polarizing filters, an image pickup device, and an image-processing means; to an inspection apparatus for detecting defects of an insulating film for film carrier tape; to a punching apparatus for punching an insulating film for film carrier tape; and to a method for controlling a punching apparatus for punching an insulating film for film carrier tape.

2. Background Art

Film carrier tapes for mounting electronic components thereon are produced through, for example, the following procedure. An insulating film (e.g., polyimide film) is punched to form sprocket holes for conveyance, round holes for mounting solder balls or metal bumps, device holes for mounting, and other holes. After provision of copper foil of a surface of the film, the copper foil is patterned while the insulating film is conveyed by the mediation of, for example, sprocket holes, thereby forming a wiring pattern. If required, a solder resist layer is formed on the wiring pattern, or a metal plating layer is formed on terminal portions. In the production of film carrier tapes such as a BGA tape, an insulating film is punched to form holes such as round holes, and metal bumps, solder balls, or similar conductors are inserted into the round holes, whereby the wiring pattern is connected to electronic components.

Conventionally, during continuous punching of an insulating film for film carrier tape coiled by a reel or a similar part by use of a forward-feeding press or a similar means, sampling inspection during punching has been avoided, from the viewpoint of productivity. Therefore, after punching of a conveyed insulating film for film carrier tape, operators visually find defects such as dents and fins through observation under a microscope. Since the inspection is carried out visually, inspection accuracy has varied among the operators, and some operators have failed to find such defects. Thus, in some cases, defects such as dents remain in a subsequent step and, furthermore, in the products for clients.

In consideration of productivity of punched insulating film for film carrier tapes, more rigorous inspection of the defects such as dents must be carried out at the time of starting punching of coiled insulating film, at the time of replacing insulating film, at the time of terminating punching, and at the time of a periodical quality control procedure. However, when a punched insulating film for film carrier tape is dented due to debris from being lifted or similar abnormality in a punching mold during production thereof or when an insulating film for film carrier tape is dented due to a foreign matter attached on the film per se, a lot of failure pieces are not detected and must be discarded, thereby lowering production yield with respect to the starting material.

In view of the foregoing, Japanese Patent Application laid-Open (kokai) Nos. 10-288586 and 10-293018 and other documents disclose an apparatus for automatically detecting dents of a lead frame, wherein the lead frame conveyed is illuminated, image data of the lead frame are pickuped by a CCD camera, and the pickuped image is processed.

Japanese Patent Application laid-Open (kokai) No. 2000-351025 discloses a method for detecting defects (e.g., dents) of a lead frame during pressing, the method including irradiating a punched lead frame with light emitted from a light-emitting device (i.e., light-emitting diode (LED)) and receiving the light reflected at the surface of the lead frame by a photoreceptor (i.e., photodiode (PD)), thereby detecting abnormalities on a surface of the lead frame.

SUMMARY OF THE INVENTION

The present invention has been conceived with an aim to solve the problems involved in conventional techniques and is based on concepts differing from those of the conventional irregularity-detection apparatuses and irregularity-detection methods. Thus, objects of the present invention are to provide a method for inspecting an insulating film for film carrier tape, an inspection apparatus for detecting defects of an insulating film for film carrier tape, a punching apparatus for punching an insulating film for film carrier tape, and a method for controlling a punching apparatus for punching an insulating film for film carrier tape. Particularly, the objects of the invention are to provide an inspection apparatus and an inspection method for detecting defects, a punching apparatus, and a method for controlling a punching apparatus, for the purpose of immediate detection of debris from being lifted toward the surface of an insulating film for film carrier tape, which debris tends to occur during punching of the insulating film for film carrier tape by use of a punching mold, whereby the number of pieces having defects on the film surface caused by attachment of debris from being lifted or foreign matter is reduced to a minimum possible number.

The present inventors have carried out extensive studies in order to attain the aforementioned objects, and have found that the objects can be attained by irradiating a pattern-formed side and/or the opposite side of an insulating film for film carrier tape with parallel rays emitted from a light source and passing through a first polarizing filter; providing a second polarizing filter and an image pickup device such that the rays having passed through or having been reflected by the insulating film for film carrier tape pass through the second polarizing filter and are received by the image pickup device; and subjecting the image input to the image pickup device to image processing as a difference of brightness. The present invention has been accomplished on the basis of this finding.

Accordingly, in a first aspect of the present invention, there is provided a method for inspecting an insulating film for film carrier tape comprising:

irradiating an insulating film for film carrier tape with parallel rays having passed through a first polarizing filter, the insulating film having been punched and being conveyed;

causing the rays having passed through or having been reflected by the insulating film for film carrier tape to pass through a second polarizing filter;

receiving the rays having passed through the second polarizing filter, by means of an image pickup device; and subjecting the image input to the image pickup device to image processing as a difference of brightness, whereby defects of the insulating film for film carrier tape are detected.

In a second aspect of the present invention, there is provided an inspection apparatus for detecting defects of an insulating film for film carrier tape, the apparatus comprising:

a conveying means for conveying an insulating film for film carrier tape;

a light source for emitting parallel rays;

a first polarizing filter disposed between the light source and a conveying path for the insulating film for film carrier tape;

an image pickup device;

a second polarizing filter disposed between the image pickup device and the conveying path for the insulating film for film carrier tape; and an image-processing means for performing image processing of the image input to the image pickup device as a difference of brightness, wherein the insulating film for film carrier tape is irradiated with parallel rays emitted from the light source and having passed through the first polarizing filter, the rays having passed through or having been reflected by the insulating film for film carrier tape are caused to pass through a second polarizing filter; and rays having passed through the second polarizing filter are received by the image pickup device.

In a third aspect of the present invention, there is provided a punching apparatus for punching an insulating film for film carrier tape, the apparatus comprising:

a conveying means for conveying an insulating film for film carrier tape;

a punching means for punching the insulating film for film carrier tape being conveyed;

a light source for emitting parallel rays;

a first polarizing filter disposed between the light source and a conveying path for the insulating film for film carrier tape;

an image pickup device;

a second polarizing filter disposed between the image pickup device and the conveying path for the insulating film for film carrier tape;

an inspecting means for detecting, piece-by-piece, defects of the insulating film for film carrier tape through image processing of the image input to the image pickup device as a difference of brightness; and a controlling means for stopping operation of the punching apparatus when, in each of a sequence of pieces, defects are continuously detected at points falling within certain areas which are substantially equivalent to one another, wherein the insulating film for film carrier tape is irradiated with parallel rays emitted from the light source and having passed through the first polarizing filter;

the rays having passed through or having been reflected by the insulating film for film carrier tape are caused to pass through a second polarizing filter; and rays having passed through the second polarizing filter are received by the image pickup device.

In a fourth aspect of the present invention, there is provided a method for controlling a punching apparatus for punching an insulating film for film carrier tape, comprising:

punching an insulating film for film carrier tape being conveyed;

subsequently, irradiating the insulating film for film carrier tape being conveyed, with parallel rays having passed through a first polarizing filter;

causing the rays having passed through or having been reflected by the insulating film for film carrier tape to pass through a second polarizing filter;

receiving the rays having passed through the second polarizing filter, by means of an image pickup device;

subjecting the image input to the image pickup device to image processing as a difference of brightness, whereby defects of the insulating film for film carrier tape are detected piece-by-piece; and stopping operation of the punching apparatus for checking the apparatus when, in each of a sequence of pieces, defects are continuously detected at points falling within certain areas which are substantially equivalent to one another.

Through employment of the method for inspecting an insulating film for film carrier tape, the inspection apparatus, the punching apparatus for punching an insulating film for film carrier tape, and the method for controlling the punching apparatus according to the present invention, variation in inspection accuracy among the operators and inspection failure of the operators can be avoided. In addition, even when a punched insulating film for film carrier tape is dented due to debris from being lifted in a punching mold during production thereof or even when an insulating film for film carrier tape is dented due to a foreign matter attached on the film per se, the punching apparatus can be stopped to check thereof, whereby rejecting many abnormal pieces can be prevented, enhancing production yield with respect to the starting material.

BRIEF DESCRIPTION OF THE DRAWINGS

Various other objects, features, and many of the attendant advantages of the present invention will be readily appreciated as the same becomes better understood with reference to the following detailed description of the preferred embodiments when considered in connection with the accompanying drawings, in which.

DETAILED DESCRIPTION OF PREFERRED EMBODIMENTS

With reference to the attached drawings, preferred embodiments of the method for inspecting an insulating film for film carrier tape, the inspection apparatus, the punching apparatus for punching an insulating film for film carrier tape, and the method for controlling the punching apparatus according to the present invention will next be described in detail.

Figure 1:
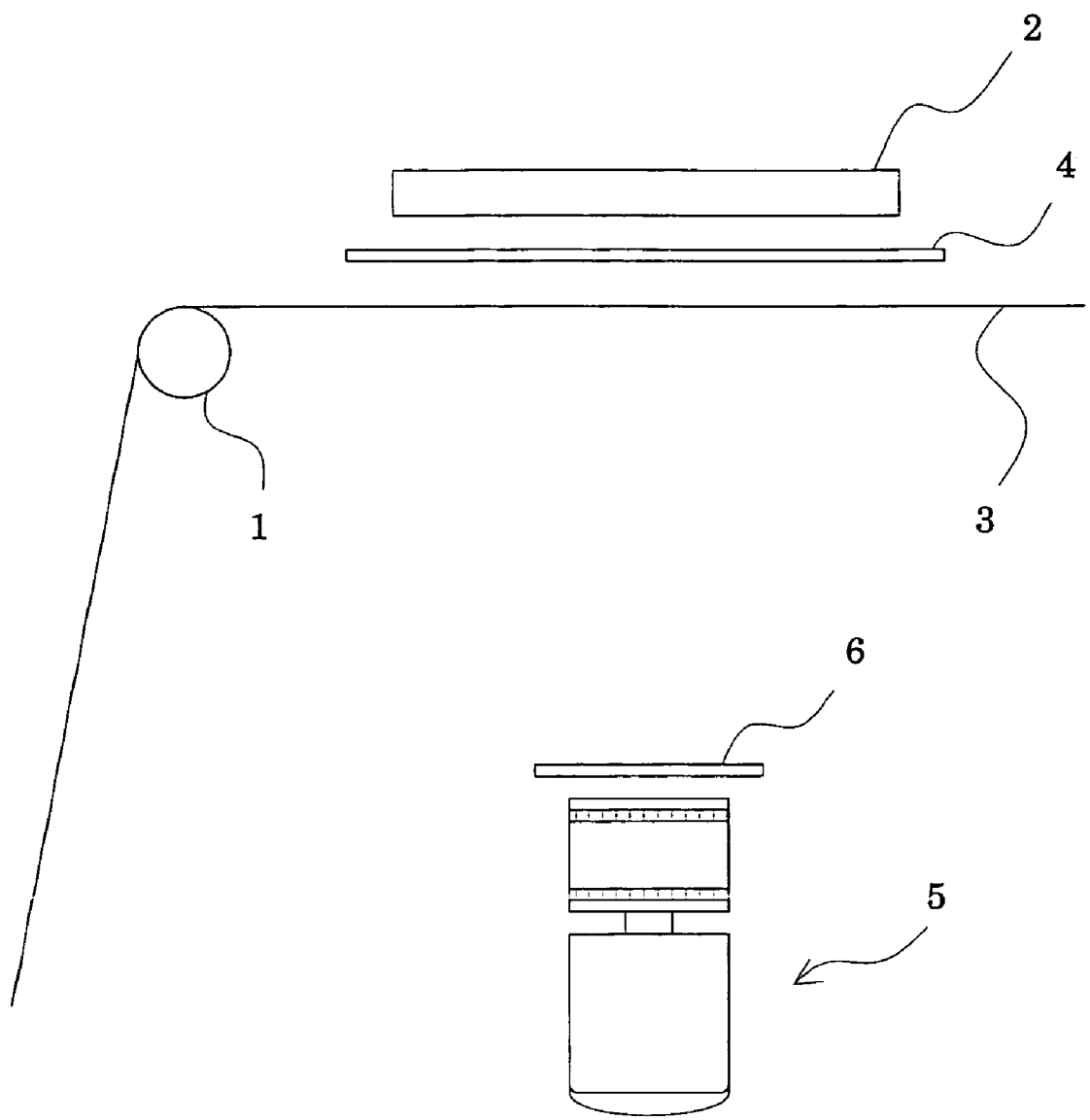
FIG. 1 is a sketch showing one embodiment of the present invention.

FIG. 1 shows an inspection apparatus for detecting defects present inside or on the top surface or the bottom surface of an insulating film 3 for film carrier tape, the apparatus comprising: a conveying means 1 (e.g. a roller) for conveying the insulating film 3 for film carrier tape; a light source 2 (e.g., an LED) for emitting parallel rays; a first polarizing filter 4 disposed between the light source 2 and a conveying path for the insulating film 3 for film carrier tape; an image pickup device 5 (e.g., a CCD camera); a second polarizing filter 6 disposed between the image pickup device 5 and the conveying path for the insulating film for film carrier tape 3; and an image-processing means (not illustrated) for performing image processing of the image input to the image pickup device 5 as a difference of brightness, wherein the insulating film 3 for film carrier tape is irradiated with parallel rays emitted from the light source and having passed through the first polarizing filter 4, the rays having passed through the insulating film 3 for film carrier tape are caused to pass through a second polarizing filter 6; and rays having passed through the second polarizing filter 6 are received by the image pickup device 5.

When inspection is carried out by means of the inspection apparatus shown in FIG. 1, an optically transparent insulating film is irradiated with, for example, red parallel rays emitted from an LED and passing through the first polarizing filter 4, the insulating film having been punched and being conveyed. The insulating film is preferably a synthetic resin film exhibiting excellent heat resistance, resistance to chemicals, stability to humidity and heat, and other properties. Examples of the synthetic resin film include polyimide film, polyamide-imide film, heat-resistant polyester film, BT resin film, phenolic resin film, and liquid crystal polymer film. Of these, polyimide film is particularly preferred, by virtue of excellent heat resistance, resistance to chemicals, stability to humidity and heat. The rays having passed through the insulating film 3 for film carrier tape is caused to pass through the second polarizing filter 6, and received by means of the image pickup device 5 (e.g., a CCD image. pickup device (CCD camera)). The image input to the image pickup device 5 is subjected to image processing as a difference of brightness (image-processing member is not illustrated), whereby defects present inside or on the top surface or the bottom surface of the insulating film 3 for film carrier tape are detected.

Figure 2:
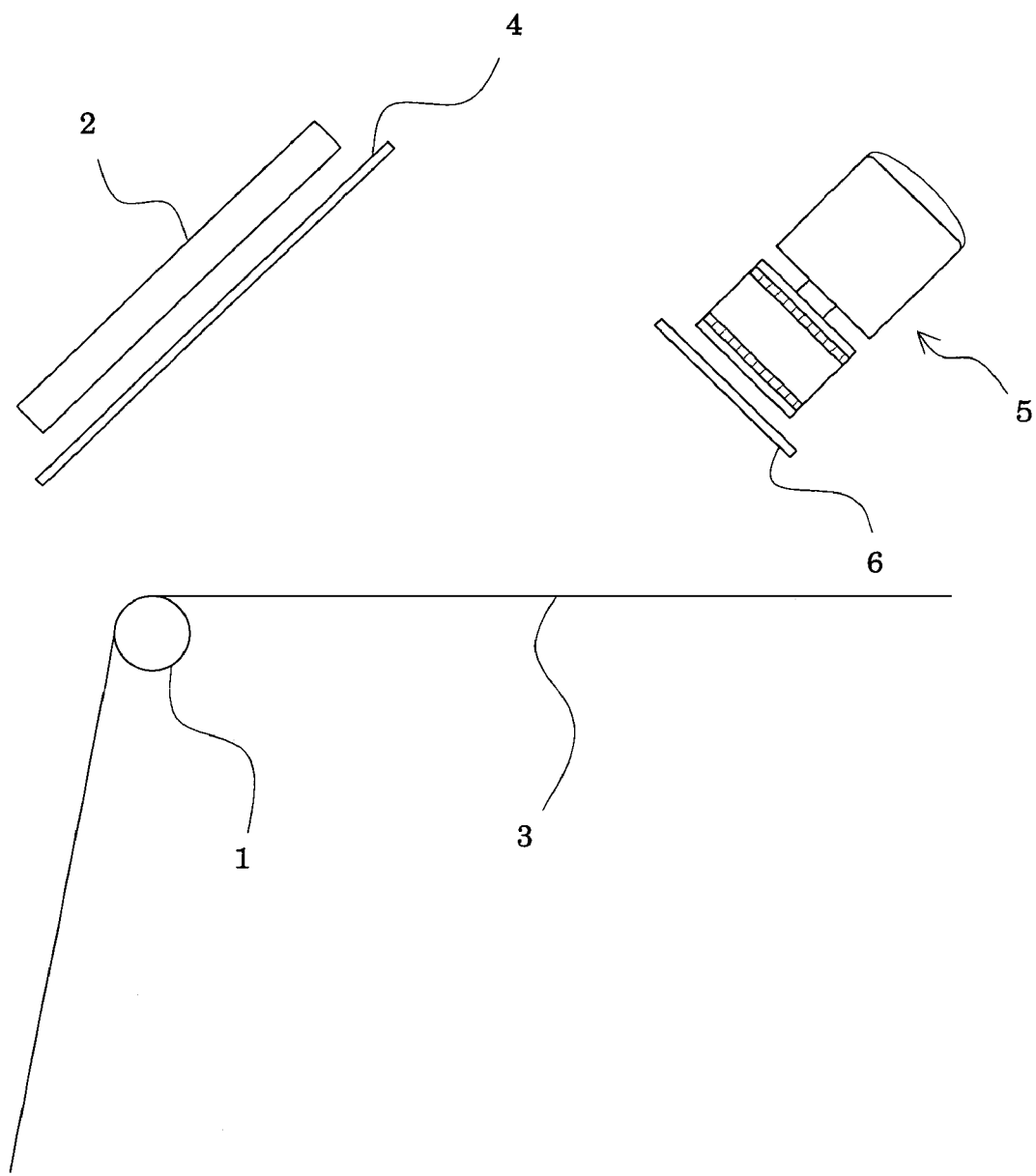
FIG. 2 is a sketch showing another embodiment of the present invention.

FIG. 2 shows an inspection apparatus for detecting defects present on the top surface of an insulating film 3 for film carrier tape, the apparatus comprising: a conveying means 1 (e.g. a roller) for conveying the insulating film 3 for film carrier tape; a light source 2 (e.g., an LED) for emitting parallel rays; a first polarizing filter 4 disposed between the light source 2 and a conveying path for the insulating film 3 for film carrier tape; an image pickup device 5 (e.g., a CCD camera); a second polarizing filter 6 disposed between the image pickup device 5 and the conveying path for the insulating film for film carrier tape 3; and an image-processing means (not illustrated) for performing image processing of the image input to the image pickup device 5 as a difference of brightness, wherein the insulating film 3 for film carrier tape is irradiated with parallel rays emitted from the light source and having passed through the first polarizing filter 4, the rays having been reflected by the insulating film 3 for film carrier tape are caused to pass through a second polarizing filter 6; and rays having passed through the second polarizing filter 6 are received by the image pickup device 5.

When inspection is carried out by means of the inspection apparatus shown in FIG. 2, an optically non-transparent laminated film 3 (e.g., polyimide film/copper foil bi-layer film or polyimide film/adhesive/copper foil tri-layer film) for film carrier tape or an optically semi-transparent insulating film 3 for,film carrier tape is irradiated with, for example, an LED light-beam (preferably black parallel rays), a UV ray, or a laser beam passing through the first polarizing filter 4, the insulating film having been punched and being conveyed. The rays having been reflected by the insulating film 3 for film carrier tape is caused to pass through the second polarizing filter 6, and received by means of the image pickup device 5 (e.g., a CCD image pickup device (CCD camera)). The image input to the image pickup device 5 is subjected to image processing as a difference of brightness (image-processing member is not illustrated), whereby defects present on the top surface of the insulating film 3 for film carrier tape are detected. Needless to say, if two sets of inspection apparatuses shown in FIG. 2 are employed, the top surface and the bottom surface of the insulating film for film carrier tape can be inspected in a single conveying step.

The parallel rays are aligned through the first polarizing filter 4. When the thus-aligned rays are not refracted through the insulating film 3 for film carrier tape (i.e., when the insulating film 3 for film carrier tape has no defects inside or on the top surface or the bottom surface thereof in the case where inspection is performed by means of the inspection apparatus shown in FIG. 1, or when the insulating film 3 for film carrier tape has no defects on the top surface thereof in the case where inspection is performed by means of the inspection apparatus shown in FIG. 2), the rays are intercepted by the second polarizing filter 6, and cannot reach the image pickup device 5. In contrast, when the insulating film 3 for film carrier tape has defects inside or on the top surface or the bottom surface thereof in the case where inspection is performed by means of the inspection apparatus shown in FIG. 1, or when the insulating film 3 for film carrier tape has defects on the top surface thereof in the case where inspection is performed by means of the inspection apparatus shown in FIG. 2, the rays aligned through the first polarizing filter 4 are disordered by the defects. Thus, the rays pass through the second polarizing filter 6 and reach the image pickup device 5. In other words, when the insulating film 3 for film carrier tape is defect-free, the defect-free portion is imaged as a dark image in the image pickup device 5 through interception of the rays by the second polarizing filter 6, whereas when the insulating film 3 for film carrier tape has a portion having defects such as dents, the portion is imaged as a bright image in the image pickup device 5 as a result of passage of the rays through the second polarizing filter 6. The difference of brightness is amplified through image processing, whereby defects such as dents present on the surface of the insulating film 3 for film carrier tape are detected.

More specifically, the area of the image corresponding to a defect-free film portion assumes gray, whereas that corresponding to a film portion having defects such as dents assumes white. When the difference of brightness between the two areas is equal to or higher than an arbitrary threshold contrast value and the area of an island-like white image is equal to or higher than a predetermined value, the area being measured by use of unit blocks (each measuring, e.g., 0.1 mm×0.1 mm) provided for the image of each piece, the insulating film is determined to have defects such as dents. In the case where defects such as dents are detected, the corresponding pieces having defects are rejected in, for example, a Subsequent step, with the assistance of a computer.

A characteristic feature of the punching apparatus of the present invention for punching an insulating film for film carrier tape is that the apparatus comprises:

a conveying means for conveying an insulating-film for film carrier tape;

a punching means for punching the insulating film for film carrier tape being conveyed;

a light source for emitting parallel rays;

a first polarizing filter disposed between the light source and a conveying path for the insulating film for film carrier tape;

an image pickup device;

a second polarizing filter disposed between the image pickup device and the conveying path for the insulating film for film carrier tape;

an inspecting means for detecting, piece-by-piece, defects of the insulating film for film carrier tape through image processing of the image input to the image pickup device as a difference of brightness; and a controlling means for stopping operation of the punching apparatus when, in each of a sequence of pieces, defects are continuously detected at points falling within certain areas which are substantially equivalent to one another, wherein the insulating film for film carrier tape is irradiated with parallel rays emitted from the light source and having passed through the first polarizing filter;

the rays having passed through or having been reflected by the insulating film for film carrier tape are caused to pass through a second polarizing filter; and rays having passed through the second polarizing filter are received by the image pickup device.

A characteristic feature of the aforementioned method for controlling a punching apparatus for punching an insulating film for film carrier tape is that the method comprises:

punching an insulating film for film carrier tape being conveyed;

subsequently, irradiating the insulating film for film carrier tape being conveyed, with parallel rays having passed through a first polarizing filter;

causing the rays having passed through or having been reflected by the insulating film for film carrier tape to pass through a second polarizing filter;

receiving the rays having passed through the second polarizing filter, by means of an image pickup device;

subjecting the image input to the image pickup device to image processing as a difference of brightness, whereby defects of the insulating film for film carrier tape are detected piece-by-piece; and stopping operation of the punching apparatus for checking the apparatus when, in each of a sequence of pieces, defects are continuously detected at points falling within certain areas which are substantially equivalent to one another.

The aforementioned punching apparatus for punching an insulating film for film carrier tape and the method for controlling the apparatus employ the aforementioned means for detecting defects such as dents and the detection method. Needless to say, the apparatus and the method may further employ other conventionally employed customary means and methods. In the aforementioned punching apparatus for punching an insulating film for film carrier tape and the method for controlling the apparatus, defects of the insulating film for film carrier tape are detected piece-by-piece, and when defects are continuously detected at points which fall within the same area in each of a sequence of pieces (e.g., five continuous pieces), operation of the punching apparatus is stopped for checking the apparatus. Therefore, rejection of a lot of abnormal pieces can be prevented, enhancing production yield with respect to the starting material.

What is claimed is:

1. A method for inspecting an insulating film for film carrier tape for mounting electronic components thereon, the method comprising:

providing a punched insulating film for film carrier tape, and conveying the insulating film via sprocket holes punched through said insulating film;

irradiating the insulating film for film carrier tape being conveyed with parallel rays having passed through a first polarizing filter;

causing the rays having passed through the insulating film for film carrier tape to pass through a second polarizing filter;

receiving the rays having passed through the second polarizing filter, by means of an image pickup device; and subjecting the image input to the image pickup device to image processing as a difference of brightness, whereby defects of the insulating film for film carrier tape are detected.

2. A method for inspecting an insulating film for film carrier tape as described in claim 1, wherein red parallel rays are employed, and the rays having passed through the insulating film for film carrier tape is caused to pass through the second polarizing filter, followed by receiving the rays by means of the image pickup device.

3. A method for inspecting an insulating film for film carrier tape as described in claim 1, wherein LED rays, UV rays, and laser beams are employed as parallel rays, and the rays having been reflected by the insulating film for film carrier tape is caused to pass through the second polarizing filter, followed by receiving the rays by means of the image pickup device.

4. A method for controlling a punching apparatus for punching an insulating film for film carrier tape for mounting electronic components thereon, the method comprising:

punching an insulating film for film carrier tape being conveyed;

subsequently, irradiating the insulating film for film carrier tape being conveyed, with parallel rays having passed through a first polarizing filter;

causing the rays having passed through or having been reflected by the insulating film for film carrier tape to pass through a second polarizing filter;

receiving the rays having passed through the second polarizing filter, by means of an image pickup device;

subjecting the image input to the image pickup device to image processing as a difference of brightness, whereby defects of the insulating film for film carrier tape are detected piece-by-piece; and stopping operation of the punching apparatus for checking the apparatus when, in each of a sequence of pieces, defects are continuously detected at points falling within certain areas which are substantially equivalent to one another.

5. A method for inspecting an insulating film for film carrier tape for mounting electronic components thereon, the method comprising:

punching an insulating film for film carrier tape, and conveying the insulating layer via sprocket holes punched through said insulating film;

subsequently, irradiating the insulating film carrier tape being conveyed, with parallel rays having passed through a first polarizing filter;

causing the rays having passed through or having been reflected by the insulating film for film carrier tape to pass through a second polarizing filter;

receiving the rays having passed through the second polarizing filter, by means of an image pickup device; and subjecting the image input to the image pickup device to image processing as a difference of brightness, whereby defects of the insulating film for film carrier tape are detected.

6. A method for inspecting an insulating film for film carrier tape for mounting electronic components thereon, the method comprising:

providing a punched insulating film for film carrier tape comprising a synthetic resin film, and conveying the insulating film via sprocket holes punched through said insulating film;

irradiating the insulating film for film carrier tape being conveyed with parallel rays having passed through a first polarizing filter;

causing the rays having passed through the insulating film for film carrier tape to pass through a second polarizing filter;

receiving the rays having passed through the second polarizing filter, by means of an image pickup device; and subjecting the image input to the image pickup device to image processing as a difference of brightness, whereby defects of the insulating film for film carrier tape are detected.

* * * * *